(12) United States Patent
Gingras et al.

(10) Patent No.: US 8,709,096 B2
(45) Date of Patent: Apr. 29, 2014

(54) TISSUE REPAIR IMPLANT

(75) Inventors: Peter Gingras, Galway (IE); Gabriela Voskerician, Beachwood, OH (US); Michael F. White, Co Sligo (IE)

(73) Assignee: Proxy Biomedical Limited, Galway (IE)

( * ) Notice: Subject to any disclaimer, the term of this patent is extended or adjusted under 35 U.S.C. 154(b) by 0 days.

(21) Appl. No.: 12/432,314

(22) Filed: Apr. 29, 2009

(65) Prior Publication Data

US 2010/0082114 A1    Apr. 1, 2010

Related U.S. Application Data (60) Provisional application No. 61/048,816, filed on Apr. 29, 2008.

(51) Int. Cl.
*A61F 2/02* (2006.01)
(52) U.S. Cl.
USPC ........................................ 623/23.76
(58) Field of Classification Search
USPC ............................ 623/23.71–23.76
See application file for complete search history.

(56) References Cited

U.S. PATENT DOCUMENTS

| | | | |
|---|---|---|---|
| 4,218,782 A * | 8/1980 | Rygg | 623/2.15 |
| 4,755,593 A * | 7/1988 | Lauren | 530/356 |
| 4,902,508 A | 2/1990 | Badylak et al. | |
| 4,956,178 A | 9/1990 | Badylak et al. | |
| 5,336,616 A | 8/1994 | Livesey et al. | |
| 5,397,353 A | 3/1995 | Oliver et al. | |
| 5,460,962 A | 10/1995 | Kemp | |
| 5,711,969 A | 1/1998 | Patel et al. | |
| 5,733,337 A | 3/1998 | Carr, Jr. et al. | |
| 5,788,625 A | 8/1998 | Plouhar et al. | |
| 5,922,028 A | 7/1999 | Plouhar et al. | |
| 6,068,837 A * | 5/2000 | Shockley et al. | 424/93.21 |
| 6,152,142 A | 11/2000 | Tseng | |

(Continued)

FOREIGN PATENT DOCUMENTS

| | | |
|---|---|---|
| EP | 0 738 106 | 8/2001 |
| EP | 1 082 057 | 2/2009 |

(Continued)

OTHER PUBLICATIONS

Extended European Search Report; Application No. 09159131.3-1219/2113262; mailed Feb. 16, 2010; 6 pages.

(Continued)

*Primary Examiner* — Suzette J Gherbi
(74) *Attorney, Agent, or Firm* — Fish & Richardson P.C.

(57) ABSTRACT

Described herein are tissue repair implants comprising at least a first layer of peritoneal membrane. The first layer of peritoneal membrane can be located adjacent to a second layer of peritoneal membrane and can be in direct contact with the second layer of peritoneal membrane. Additional layers (e.g., a third or fourth layer) can be included. Where more than one layer is present, the layers can be affixed to one another. For example, a first layer of peritoneal membrane can be attached to the second layer of peritoneal membrane by an adhesive bond, suture, or staple. One or more of the peritoneal membranes can be non-crosslinked, partially crosslinked, or substantially fully crosslinked. Any of the layers of peritoneal membrane may be attached to a wall (e.g., an interior or exterior wall) of an abdominal tissue by an adhesive, suture, and/or staples.

13 Claims, 7 Drawing Sheets

(56) References Cited

U.S. PATENT DOCUMENTS

| | | |
|---|---|---|
| 6,206,931 B1 | 3/2001 | Cook et al. |
| 6,312,474 B1 | 11/2001 | Francis et al. |
| 6,358,284 B1 | 3/2002 | Fearnot et al. |
| 6,398,819 B1 | 6/2002 | Bell |
| 6,468,313 B1 | 10/2002 | Claeson et al. |
| 6,579,307 B2 | 6/2003 | Sarac |
| 6,638,312 B2 | 10/2003 | Plouhar et al. |
| 6,652,594 B2 | 11/2003 | Francis et al. |
| 6,666,892 B2 | 12/2003 | Hiles et al. |
| 6,866,686 B2 | 3/2005 | Ollerenshaw et al. |
| 7,060,103 B2 | 6/2006 | Carr, Jr. et al. |
| 7,121,999 B2 * | 10/2006 | Abraham et al. ............. 600/36 |
| 7,129,035 B2 | 10/2006 | Goldstein et al. |
| 7,144,588 B2 | 12/2006 | Oray et al. |
| 7,318,998 B2 | 1/2008 | Goldstein et al. |
| 7,824,420 B2 * | 11/2010 | Eldridge et al. ............. 606/151 |
| 2003/0100955 A1 | 5/2003 | Greenawalt et al. |
| 2003/0130747 A1 * | 7/2003 | Abraham et al. ........... 623/23.72 |
| 2003/0225355 A1 | 12/2003 | Butler |
| 2004/0034418 A1 | 2/2004 | Lie et al. |
| 2004/0107006 A1 | 6/2004 | Francis et al. |
| 2005/0107868 A1 * | 5/2005 | Nakayama et al. ........... 623/1.39 |
| 2005/0153442 A1 * | 7/2005 | Katz et al. ..................... 435/366 |
| 2005/0191281 A1 | 9/2005 | Ollerenshaw et al. |
| 2006/0064175 A1 | 3/2006 | Pelissier et al. |
| 2006/0159664 A1 | 7/2006 | Pandit et al. |
| 2006/0253188 A1 * | 11/2006 | Case .............................. 623/1.24 |
| 2007/0250177 A1 * | 10/2007 | Bilbo ........................... 623/23.72 |
| 2008/0009667 A1 | 1/2008 | Longhini et al. |
| 2008/0027542 A1 | 1/2008 | McQuillan et al. |
| 2008/0097601 A1 * | 4/2008 | Codori-Hurff et al. ............. 623/8 |
| 2010/0030259 A1 * | 2/2010 | Pavcnik et al. ................ 606/215 |
| 2010/0234878 A1 * | 9/2010 | Hruska et al. ................. 606/213 |

FOREIGN PATENT DOCUMENTS

| | | | |
|---|---|---|---|
| EP | 1 082 071 | | 3/2009 |
| EP | 1 083 828 | | 3/2009 |
| WO | WO 99/19005 | | 4/1999 |
| WO | WO 99/62427 | | 12/1999 |
| WO | WO 2004/008997 | | 1/2004 |
| WO | WO2005023321 | * | 3/2005 |
| WO | WO 2006/121887 | | 11/2006 |
| WO | WO 2007/076508 | | 7/2007 |
| WO | WO 2007/134134 | | 11/2007 |
| WO | WO 2008/134610 | | 11/2008 |

OTHER PUBLICATIONS

Extended European Search Report; Application No. 09159120.6-1219/2113261; mailed Oct. 13, 2009; 8 pages.

European Office Action; Application No. 09159120.6; mailed Feb. 22, 2011; 7 pages.

Liang et al., "Effects of Crosslinking Degree of an Acellular Biological Tissue on its Tissue Regeneration Pattern," Biomaterials 25:3541-3552, 2004.

USPTO Office Action; U.S. Appl. No. 12/432,405; mailed Apr. 29, 2011; 9 pages.

Fish & Richardson P.C. Response to Office Action of Apr. 29, 2011, U.S. Appl. No. 12/432,405, filed Oct. 31, 2011; 6 pages.

USPTO Office Action; U.S. Appl. No. 12/432,405; mailed Feb. 1, 2012; 12 pages.

Fish & Richardson P.C. Notice of Appeal, U.S. Appl. No. 12/432,405, filed Aug. 1, 2012; 1 page.

Fish & Richardson P.C. Request for Continued Examination, U.S. Appl. No. 12/432,405, filed Mar. 1, 2013; 10 pages.

* cited by examiner

TISSUE REPAIR IMPLANT

CROSS-REFERENCE TO RELATED APPLICATIONS

This application claims the benefit of the priority date of U.S. Application No. 61/048,812, which was filed Apr. 29, 2008. The content of this prior application is hereby incorporated by reference in its entirety.

TECHNICAL FIELD

This invention relates to a tissue repair implant. and more particularly to an implant that includes one or more layers of peritoneal membranes.

SUMMARY

According to the invention, there is provided a tissue repair implant comprising a first layer of peritoneal membrane and a second layer of peritoneal membrane.

The layer of peritoneal membrane acts to help prevent adhesion of internal organs or tissue structures while providing a template for native peritoneum regeneration. By providing a plurality of layers of peritoneal membrane, this arrangement increases the mechanical strength of the implant along with providing a more ideal template for native peritoneum regeneration. Such an approach may eliminate the need for an alternative biologic non-peritoneal derived tissue.

According to the invention, there is provided a tissue repair implant that includes one or more layers of peritoneal membranes and/or one or more layers of tissues that include peritoneal membranes.

The peritoneal membrane is made of a thin layer of epithelial cells, which is called mesothelium because the epithelial cells are of mesodermal origin. The mesothelium is supported by a thin layer of connective tissue, and the implants of the invention can include the peritoneal membrane, or mesothelium, alone or supported by the connective tissue with which it is naturally associated. In either event, the implant can include a support member, as described further below. As noted, the implant can also include one or more layers of tissues that include peritoneal membranes. When harvested from the abdominal wall of an animal (e.g., a warm blooded vertebrate), the tissue can include the peritoneal membrane, associated connective tissue, such as adipose tissue, and it may also include muscle cells, other cells (e.g., immune cells or bacteria) and fascia (e.g., two fascia layers). Prior to incorporation into the implant, the tissue can be processed to remove some or essentially all of the associated cells, including muscle cells, bacterial cells, and fat cells. The post-harvesting processing can also include a screen for agents such as viruses (e.g., Hepatitis B) and/or cleansing or sterilization of the tissue to remove infectious agents. After processing of the tissue, the fascia can remain to enhance mechanical strength. For example, two layers of fascia can merge or be compressed into a single layer of fascia that enhances the mechanical strength of the peritoneal membrane along both axes. Processing can also increase the collagen content or concentration and reduce the levels of toxins relative to the amounts present before harvesting.

In one embodiment of the invention, the first layer of peritoneal membrane is located adjacent to the second layer of peritoneal membrane. The first layer of peritoneal membrane may be in direct contact with the second layer of peritoneal membrane. The implant may comprise a fastener or means to attach the first layer of peritoneal membrane to the second layer of peritoneal membrane. The fastener or attachment means may comprise an adhesive bond. The implant may comprise a laminate of the first layer of peritoneal membrane and the second layer of peritoneal membrane.

At least one of the layers of peritoneal membrane may be non-crosslinked. The non-crosslinked layer of peritoneal membrane resists being remodelled by surrounding tissue. At least one of the layers of peritoneal membrane may be partially crosslinked. The partially crosslinked layer of peritoneal membrane resists being remodelled by surrounding tissue. At least one of the layers of peritoneal membrane may be substantially fully crosslinked. The crosslinked layer of peritoneal membrane is remodelled by surrounding tissue. The first layer of peritoneal membrane may be non-crosslinked or partially crosslinked, and the second layer of peritoneal membrane can be substantially fully crosslinked. The implant may comprise a third layer of peritoneal membrane. The first layer of peritoneal membrane may be non-crosslinked or is partially crosslinked, the second layer of peritoneal membrane may be substantially fully crosslinked, and the third layer of peritoneal membrane is non-crosslinked or may be partially crosslinked. The second layer of peritoneal membrane may be located between the first layer of peritoneal membrane and the third layer of peritoneal membrane.

In another embodiment, the layer of peritoneal membrane is configured to be remodelled by in-growth of tissue. The multilayer peritoneal membrane construct may be configured to be remodelled by in-growth of surrounding peritoneum. The layer of peritoneal membrane may comprise means to promote in-growth of tissue. The layer of peritoneal membrane may comprise a plurality of pores.

In one case, the layer of peritoneal membrane comprises means to promote fluid communication.

In one case, the layer of peritoneal membrane is configured to be attached to a tissue wall. The multilayer peritoneal membrane construct may be configured to be attached to a tissue wall. The layer of peritoneal membrane may be configured to be attached to an interior wall of an abdominal tissue. The implant may comprise a fastener or means to attach the layer of peritoneal membrane to a tissue wall. The fastener or attachment means may comprise a suture element, and/or a staple element, and/or an adhesive.

In another case, the implant is configured to treat an abdominal hernia repair, and/or a pelvic floor reinforcement, and/or a vaginal reconstruction, and/or a uterine wound cover, and/or a colorectal application, and/or a urological application, and/or a gynecological application. The shape of the implant may be pre-defined to suit the shape of an abdominal cavity.

In one case, the layer of peritoneal membrane is derived from a segment of an abdominal wall of a warm blooded vertebrate. The layer of peritoneal membrane may be delaminated from the abdominal wall of the warm blooded vertebrate. The layer of peritoneal membrane may comprise an allograft membrane derived from a human donor. The layer of peritoneal membrane may comprise a xenograft membrane derived from an animal. The layer of peritoneal membrane may comprise a bovine or porcine membrane. The layer of peritoneal membrane may be derived from a porcine sow source. The layer of peritoneal membrane may be sterilised. The layer of peritoneal membrane may be decellularised. The layer of peritoneal membrane may be lyophilised.

In another case, the layer of peritoneal membrane comprises interrupted sutures to retain compliance.

In one embodiment, the layer of peritoneal membrane is oriented with the mesothelium surface oriented in an outward direction on organ contacting surfaces.

In another aspect of the invention there is provided a graft prosthesis comprising: a purified, collagen based matrix removed from a peritoneal membrane source, the purified structure having a low endotoxin level (i.e., a contaminant level making the purified structure biocompatible).

According to the invention there is provided a tissue repair implant comprising a membrane of peritoneal tissue.

The implant assists in tissue repair by providing additional mechanical strength to the abdominal wall. For example, in the case of a wound opening by covering the wound opening with the implant while reinforcing the wound. The in-growth of surrounding abdominal wall tissue into the implant further improves the wound healing.

The implant will come into contact with the bowel and internal organs. The peritoneal tissue acts to minimise or discourage organ adhesion to the implant.

In one embodiment of the invention, the membrane of peritoneal tissue is configured to be attached to an interior wall of an abdominal tissue. Preferably, the implant comprises means to attach the membrane of peritoneal tissue to an interior wall of an abdominal tissue. For example, the attachment means comprises a suture element, and/or a staple element. The implant can be configured to treat or repair an abdominal hernia, and/or for pelvic floor reinforcement, and/or a vaginal reconstruction, and/or as a uterine wound cover, and/or in colorectal applications, urological applications, or gynecological applications.

In one case, the shape of the implant is pre-defined to suit the shape of an abdominal cavity.

In another embodiment, the membrane of peritoneal tissue is derived from a segment of an abdominal wall of a warm blooded vertebrate. Preferably, the membrane of peritoneal tissue is delaminated from the abdominal wall of the warm blooded vertebrate. The membrane of peritoneal tissue may comprise an allograft membrane derived from a human donor. The membrane of peritoneal tissue may comprise a xenograft membrane derived from an animal. Preferably, the membrane of peritoneal tissue comprises a bovine or porcine membrane.

In another case, the membrane of peritoneal tissue is sterilised. Preferably, the membrane of peritoneal tissue is lyophilised.

In one embodiment, the implant comprises a support member to reinforce the membrane of peritoneal tissue. In the case where there is large strength requirement, for example in the case of a large opening during hernia repair, the support member provides additional strength. In the case where there is less or no load bearing, for example in colorectal or women's health applications, the support member may not be required. Preferably, the support member comprises a mesh. The support member may comprise a non-biological material. The support member may comprise a synthetic material. The support member may comprise a biodegradable material.

In one case, the implant comprises a fastener or means to attach the membrane of peritoneal tissue to the support member. Preferably, the support member is at least partially encapsulated in the membrane of peritoneal tissue. Ideally, the implant comprises a first membrane layer of peritoneal tissue and a second membrane layer of peritoneal tissue. Most preferably, the support member is located between the first membrane layer of peritoneal tissue and the second membrane layer of peritoneal tissue.

In another embodiment, the support member comprises at least one opening extending at least partially therethrough. Preferably, the membrane of peritoneal tissue extends at least partially through the opening of the support member to attach the membrane of peritoneal tissue to the support member. The support member can comprise means to grip the membrane of peritoneal tissue extending at least partially through the opening.

In another case, the attachment means comprises a suture element, and/or a staple element. The membrane of peritoneal tissue may be bonded to the support member. The membrane of peritoneal tissue may be lyophilised to the support member. The membrane of peritoneal tissue may be attached to the support member by means of electrospinning.

In one embodiment, the implant is configured to carry one or more biologically active agents. Preferably, the membrane of peritoneal tissue is configured to carry one or more biologically active agents.

In one case, the implant is movable between a delivery configuration and a deployment configuration. Preferably the implant is substantially collapsed in the delivery configuration and substantially expanded in the deployment configuration. The implant can comprise means to bias the implant towards the deployment configuration. The biasing means may comprise a biodegradable material. Thus, the implant can assume various configurations and can be manipulated by hand to assume a deployment configuration in which it is folded, compacted, or substantially collapsed (to facilitate delivery to a patient). Upon administration to a patient, the implant can be moved into, or allowed to assume, a delivery configuration in which it is expanded and will often be essentially flat; a sheet.

In another aspect of the invention there is also provided a method of preparing a tissue repair implant of the invention.

In one embodiment of the invention, the method comprises the step of shaping the implant to suit the shape of an abdominal cavity or targeted region of application.

In one case, the method comprises the step of providing or deriving the membrane of peritoneal tissue from a segment of an abdominal wall of a warm blooded vertebrate. Accordingly, the layer of peritoneal membrane may comprise a porcine membrane derived from a sow.

In another embodiment, the method comprises the step of sterilising the membrane of peritoneal tissue.

In another case, the method comprises the step of attaching the membrane of peritoneal tissue to a support member. Preferably, the method comprises the step of at least partially extending the membrane of peritoneal tissue through an opening of the support member. The membrane of peritoneal tissue may be drawn through the opening of the support member. The membrane of peritoneal tissue may be pushed through the opening of the support member. The membrane of peritoneal tissue may be extended through the opening of the support member by application of a pressure differential. The membrane of peritoneal tissue may be extended through the opening of the support member by application of a mechanical force.

In one embodiment, the method comprises the step of at least partially encapsulating the support member in the membrane of peritoneal tissue. The membrane of peritoneal tissue may be bonded to the support member. The membrane of peritoneal tissue may be lyophilised to the support member. The membrane of peritoneal tissue may be attached to the support member by means of electrospinning.

The invention also provides in a further aspect a method of repairing tissue, the method comprising the step of attaching an implant as described herein or a membrane of peritoneal tissue therein to an interior wall of the tissue.

In one embodiment of the invention, the method comprises a method of repairing an abdominal tissue. The method may comprise a method of treating an abdominal hernia repair, and/or a pelvic floor reinforcement, and/or a vaginal reconstruction, and/or a uterine wound cover, and/or a colorectal application, and/or a urological application, and/or a gynecological application.

In one case, the method comprises the step of delivering the membrane of peritoneal tissue to a deployment site at the interior wall of the tissue. Preferably, the membrane of peritoneal tissue is delivered laparoscopically. Ideally, the method comprises the step of collapsing the membrane of peritoneal tissue to a delivery configuration prior to the step of delivery. Most preferably, the method comprises the step of causing expansion of the membrane of peritoneal tissue to a deployment configuration after the step of delivery.

According to a further aspect of the invention, there is provided an apparatus for (grafting) repairing the abdominal wall, the abdominal wall having an inside surface that defines a cavity for containing the internal organs, the apparatus comprising: a prosthetic (support) reinforcement member having inner and outer surfaces, said outer surface for engaging and adhering to the inside surface of the abdominal wall: and a layer of biologic tissue being attached to said inner surface of said prosthetic reinforcement, said layer of biologic tissue extending over a portion of the inwardly facing surface of the prosthetic reinforcement to provide resistance to adhesion formation and internal organ attachment as wound healing and tissue ingrowth into the prosthetic reinforcement occurs; said layer of biologic tissue being selected from a group consisting of peritoneal tissue.

The invention also provides in another aspect a tissue graft comprising the peritoneal membrane of a segment of the abdominal wall of a warm blooded vertebrate, the peritoneal membrane being delaminated from the abdominal wall.

According to a further aspect of the invention, there is provided a tissue graft comprising two or more layers of peritoneal membrane of a segment of the abdominal wall of a warm blooded vertebrate, the peritoneal membrane being delaminated from the abdominal wall.

The invention also provides in another aspect a collagenous biomaterial medical device, comprising: a laminate having a plurality of layers of (lyophilized) peritoneal membrane.

According to a further aspect of the invention there is provided a graft prosthesis comprising: a purified, collagen based matrix removed from a peritoneal membrane source, the purified structure having a contaminant level making the purified structure biocompatible. The purified structure can have a low endotoxin level.

The use of the biologic peritoneal membrane in laminate form offers a longer term reinforcement solution that enhances the wound healing response while preventing adhesion formation.

The biologic laminate implant which consists of multiple layers of a biological membrane provides a means of adhesion prevention, reinforcement, and augmentation which satisfies the need for tissue regeneration through hosting tissue remodelling, and displays comparable mechanical properties to the adjacent normal tissue, and prevents or reduces adhesion formation during host tissue remodelling.

The placement of the laminate of peritoneal membrane tissue of allo- or xeno-derived source, at the location of reinforcement/repair leads to superior integration compared to a synthetic mesh within the same surrounding tissue, which naturally leads to minimal/loss of fibrous encapsulation, which in turn leads to reduced implant shrinkage; and presentation of an adhesion barrier leading to minimal/lack of associated intestinal adhesions, eviscerations or chronic pain.

The peritoneal membrane can be processed to remove any immunogenic material, such as cells, viruses, and can be subjected to appropriate sterilization. The invention provides a multilayered processed and sterile peritoneal membrane laminate from either allo- or xeno-source for wound covering, and also provides a multi-layer processed and sterile peritoneal membrane from either allo- or xeno-source for reinforcement and/or repair in the absence of a synthetic mesh or other mechanical support in soft tissue repair.

In numerous embodiments, where a composition is said to comprise a certain element, it may also consist of that element.

The details of one or more embodiments of the invention are set forth in the accompanying drawings and the description below. Other features, objects, and advantages of the invention will be apparent from the description and drawings, and from the claims.

DETAILED DESCRIPTION

In this patent specification, the term "material" includes any biologically derived component that is multi-layered; the term "regeneration" is understood as the process of anatomical and physiological restoration of a tissue to, or toward, its normal structure and function; the term "bioactive" is defined as either a biological tissue of human (allograft) or xenograft source that support the process of wound healing leading to tissue regeneration; the term "micro or macro patterned" is defined as any aperture with any design, and any orientation, or puncture pattern into a bioactive material; and the term "adhesive" is understood as any chemical and/or biological bonding material or technique leading to a monolithic multi-layer structure.

A peritoneal tissue derived from a segment of an abdominal wall of a warm blooded vertebrate may comprise a peritoneal membrane, muscle, adipose tissue, and two fascia layers. The peritoneal membrane is thus one of a number of constituent parts of a peritoneal tissue.

Figure 1:
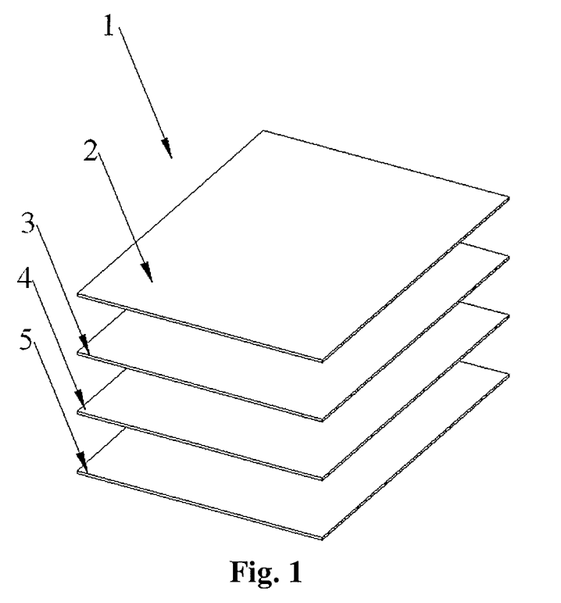
FIG. 1 is an exploded isometric view of a tissue repair implant according to the invention, with a multiple membrane layer stack up.

Referring to the drawings, and initially to FIG. 1 thereof, there is illustrated a tissue repair implant 1 according to the invention. The implant 1 may be employed to treat an abdominal hernia repair, and/or a pelvic floor reinforcement, and/or a vaginal reconstruction, and/or a uterine wound cover, and/or a colorectal application, and/or a urological application, and/or a gynaecological application.

The implant 1 comprises a first layer of peritoneal membrane 2, a second layer of peritoneal membrane 3, a third layer of peritoneal membrane 4, and a fourth layer of peritoneal membrane 5.

The implant 1 comprises a laminate of the first layer of peritoneal membrane 2, the second layer of peritoneal membrane 3, the third layer of peritoneal membrane 4, and the fourth layer of peritoneal membrane 5. The first layer of peritoneal membrane 2 is located adjacent to the second layer of peritoneal membrane 3 and is in direct contact with the second layer of peritoneal membrane 3. Similarly the second layer of peritoneal membrane 3 is located adjacent to the third layer of peritoneal membrane 4 and is in direct contact with the third layer of peritoneal membrane 4. Similarly the third layer of peritoneal membrane 4 is located adjacent to the fourth layer of peritoneal membrane 5 and is in direct contact with the fourth layer of peritoneal membrane 5. The second layer of peritoneal membrane 3 is located between the first layer of peritoneal membrane 2 and the third layer of peritoneal membrane 4. Similarly the third layer of peritoneal membrane 4 is located between the second layer of peritoneal membrane 3 and the fourth layer of peritoneal membrane 5.

The first layer of peritoneal membrane 2 is attached to the second layer of peritoneal membrane 3 by means of an adhesive bond. Similarly the second layer of peritoneal membrane 3 is attached to the third layer of peritoneal membrane 4 by means of an adhesive bond. Similarly the third layer of peritoneal membrane 4 is attached to the fourth layer of peritoneal membrane 5 by means of an adhesive bond.

Any of the layers of peritoneal membrane 2, 3, 4, 5 may be non-crosslinked, or partially crosslinked, or fully crosslinked. In this case the first layer of peritoneal membrane 2 is non-crosslinked or is partially crosslinked, the second layer of peritoneal membrane 3 is fully crosslinked, and the third layer of peritoneal membrane 4 is non-crosslinked or is partially crosslinked.

Any of the layers of peritoneal membrane 2, 3, 4, 5 may be attached to an interior wall of an abdominal tissue by means of a suture element, and/or a staple element. Any of the layers of peritoneal membrane 2, 3, 4, 5 may be remodelled by in-growth of tissue. Any of the layers of peritoneal membrane 2, 3, 4, 5 may comprise a plurality of pores to promote in-growth of tissue.

Each layer of peritoneal membrane 2, 3, 4, 5 is derived from a segment of an abdominal wall of a warm blooded vertebrate, and is delaminated from the abdominal wall of the warm blooded vertebrate. Any of the layers of peritoneal membrane 2, 3, 4, 5 may comprise an allograft membrane derived from a human donor, or may comprise a xenograft membrane derived from an animal, such as a bovine or porcine membrane. Each layer of peritoneal membrane 2, 3, 4, 5 is decellularised and is lyophilised.

The peritoneal tissue derived from the segment of the abdominal wall of the warm blooded vertebrate comprises the peritoneal membrane, muscle, adipose tissue, and two fascia layers.

The peritoneal tissue can be processed after harvesting from the abdominal wall of the warm blooded vertebrate. The processing can include removing the muscle and adipose tissue from the peritoneal tissue, screening the peritoneal tissue for viruses such as Hepatitis B, and cleaning the peritoneal tissue to remove viruses, bacteria, and the adipose tissue.

After the processing of the peritoneal tissue, the two fascia layers merge into a single fascia layer. The single fascia layer enhances the mechanical strength of the peritoneal membrane in both axes.

After the processing of the peritoneal tissue, the collagen content in all layers of the peritoneal tissue is higher and the toxin level in all layers of the peritoneal tissue is lower compared with the peritoneal tissue before processing.

In use, one or more of the layers of peritoneal membrane 2, 3, 4, 5 is attached to an interior wall of an abdominal tissue by means of the suture element, and/or the staple element. The implant 1 may thus be employed to treat an abdominal hernia repair, and/or a pelvic floor reinforcement, and/or a vaginal reconstruction, and/or a uterine wound cover, and/or a colorectal application, and/or a urological application, and/or a gynaecological application.

Over time, one or more of the layers of peritoneal membrane 2, 3, 4, 5 is likely to be remodelled by in-growth of tissue.

Figure 2:
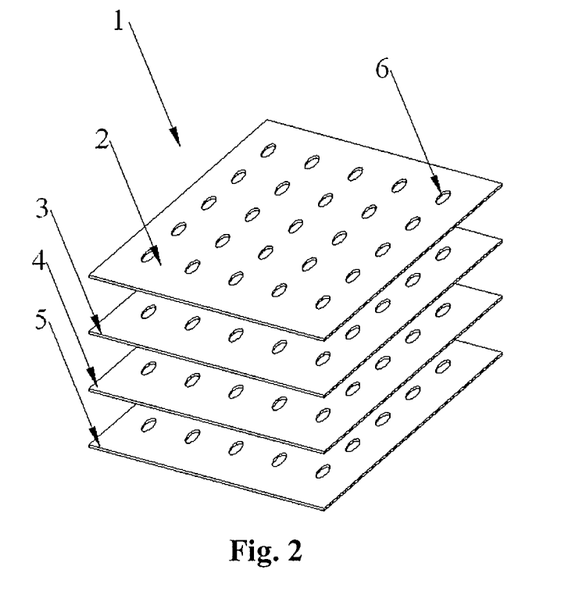
FIG. 2 is an exploded isometric view of a tissue repair implant according to the invention, with a multiple membrane layer stack up with perforated membranes.
Figure 3:
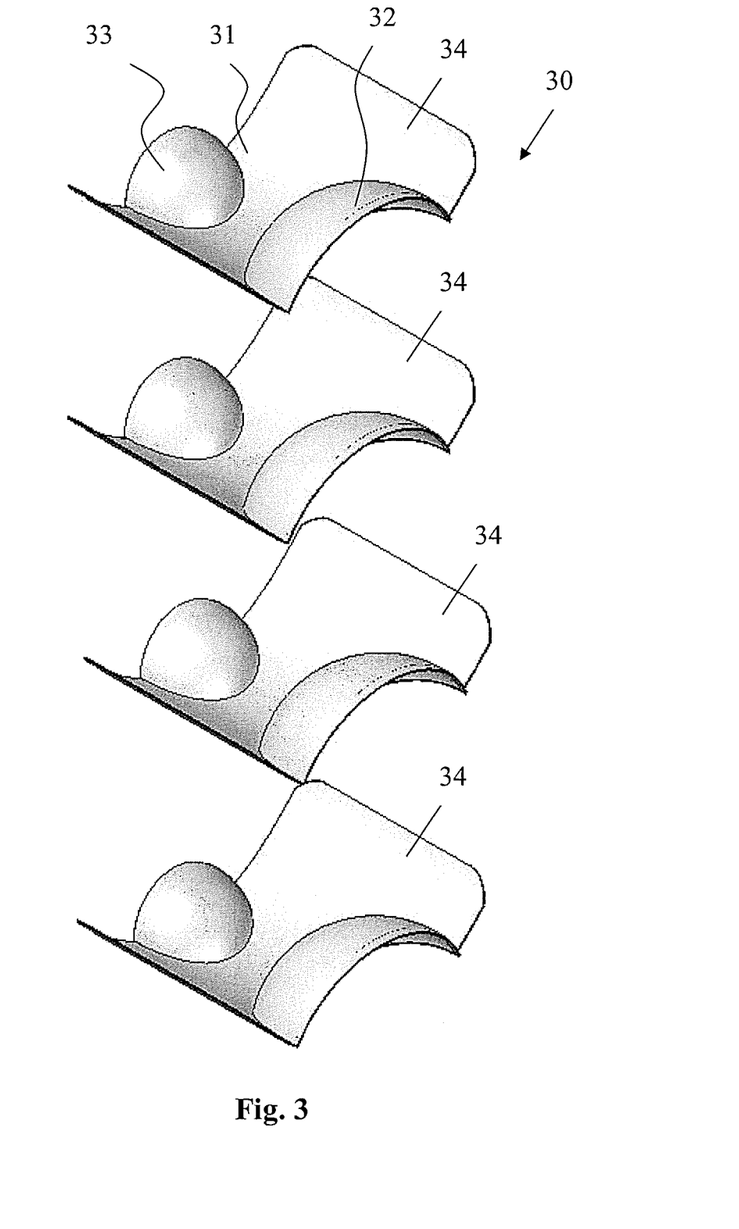
FIG. 3 is an exploded isometric view of a tissue repair implant according to the invention with the preformed implant comprising multiple preformed peritoneal membrane layers.

Referring to FIG. 2 there is illustrated another tissue repair implant 30 according to the invention, which is similar to the tissue repair implant 1 of FIG. 1, and similar elements in FIG. 2 are assigned the same reference numerals.

The implant 30 is formed to a predefined shape to suit the area of application. The implant 30 comprises multiple layers of peritoneal membrane 34 which are formed to match the profile of a hysterectomised pelvic floor with curves to match the pelvic floor 31, bladder 32 and rectum 33

It will be appreciated that the layers of peritoneal membrane may be attached together by a variety of fasteners or possible means of attachment, such as:

1. Membrane Manipulation to Achieve Membrane Attachment

This concept involves the manipulation of an underlying membrane to allow attachment of a subsequent membrane onto it.

An embodiment of this concept involves the cutting of a number of lines into the underlying membrane which correspond to a strip located on the outermost membrane. These cuts in combination with the strip will be used to weave all the layers together. In a second embodiment, one or more small designated areas of the membrane is inserted through one or more apertures in the underlying membrane. Upon recovery of the underlying membranes, the membrane will be clamped in place by the recovering underlying membrane.

2. Mechanical Attachment Using Suturing or Stapling

The laminate may be achieved through the use of a suturing method whereby a suitable filament is passed through the multiple layers in a specific pattern. This may be achieved through a running or point suturing method.

Attachment of the membrane may be achieved through the use of a suturing or stapling method while the membrane may have an inherent porosity suited to a specific suturing/stapling pattern.

3. Mechanical Attachment of Membranes Through the Use of an Inherently Adhesive Material In order to achieve an adequate bond, an adhesive membrane may be used. In the case of a biological membrane, the multilayer bonding may take advantage of alginates, possibly in a lyophilized form, to impart an adequate amount of adhesive properties.

4. Use of a Synthetic/Biological Adhesive

An adhesive may be used to bond the membranes together. In order to attach the biological membrane to another biological membrane, a biologic adhesive for example glutaraldehyde based or a synthetic adhesive may be used.

5. Suturing/Sewing Attachment

This method involves the use of a running suture/sew around the perimeter of the multilayered structure to attach the membranes together. In addition, a single point or running suture/sew may also be used to attach the membranes over the entire surface. A suture/sew guide may also be provided which allows for easy and consistent line-up of the membranes when sewing.

6. Lyophilisation of Membranes Either Compressed Together or Separate

This method involves the use of freeze-drying of the membranes together. Lyophilisation of the biologic membranes together at specific points allows for the connection of the two membrane components. In order for this to occur successfully, the two layers of biological membrane may need to be pressed together so vacuum packing may be required.

According to the invention, a laminate biological implant material has been developed for regenerating, reinforcing, or augmenting soft tissue defects in a patient. The laminate biological implant may consist of multiple layers of a bioactive and flexible material construct. Such an approach matches the predictable and reliable mechanical properties of a synthetic mesh with the regenerative characteristics of mechanically weaker, yet biologically active materials. The encapsulating bioactive material could be micro or macro patterned to allow physiological fluid transport and enhance tissue incorporation, depending on the specific application.

According to the invention a laminate biological implant has been developed to meet criteria for wound covering, tissue reinforcement, and augmentation. In particular, a biologic membrane laminate with adequate mechanical support and the ability to stimulate tissue regeneration are features of the laminate. The present invention addresses the shortcomings of current reinforcement and augmentation solutions related to general, ob/gyn, and colo-rectal surgery. The biologic membrane may be peritoneal membrane from an allograft or xenograft source. In one embodiment, the biologic membrane is used to create a bilayer structure for use as a wound covering on pelvic floor and abdominal wall defects. In another embodiment, a biological membrane laminate is created through mechanical means. In another embodiment, apertures can be created within the laminate to allow for fluid transport.

EXAMPLES

Example 1

Determination of a Suitable Membrane for Adhesion Prevention

Figure 4:
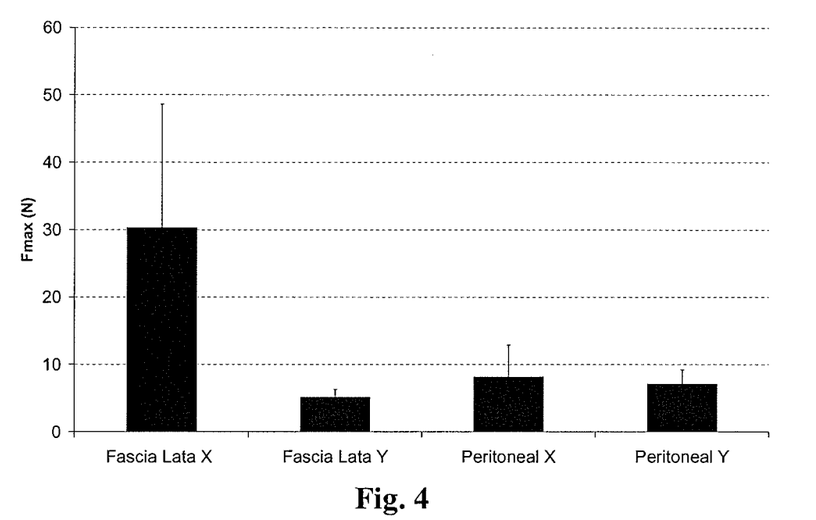
FIG. 4 is a graph showing the tensile strength of processed human fascia lata and processed human peritoneal membrane in both the X and Y directions.

Two membranes were chosen as potential adhesion preventing membranes. Both peritoneal membrane and fascia lata were chosen due to their natural anti-adhesion anatomy. The mechanical properties of each membrane was investigated. It was found that peritoneal membrane behaves more isotropic than fascia lata, hence proving more appropriate as a soft tissue implant. FIG. 4 illustrates the tensile testing results.

Example 2

Isolation of a Suitable Population for Membrane Sourcing

Figure 5:
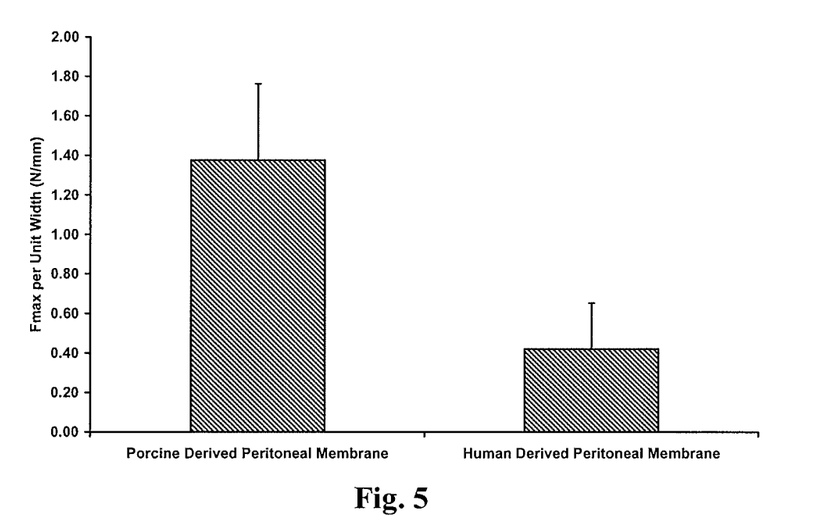
FIG. 5 is a graph showing the differences in useable surface area of peritoneal membrane between porcine derived peritoneal membrane and human derived peritoneal membrane.
Figure 6:
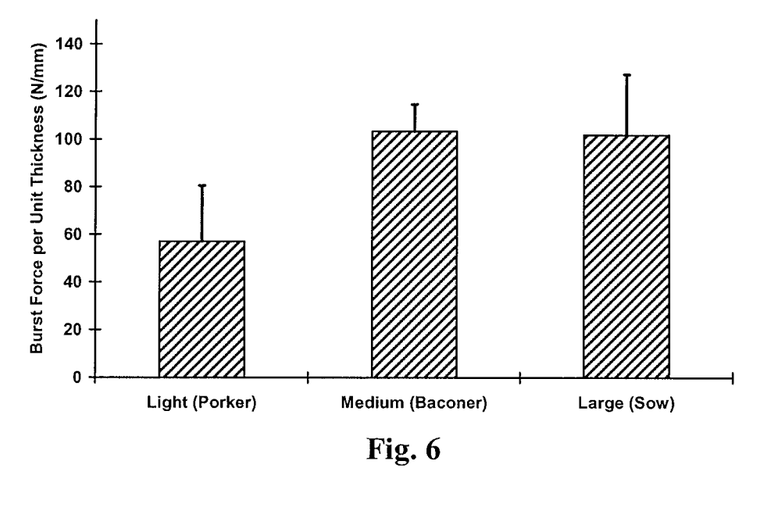
FIG. 6 is a graph showing the average burst strength of porcine derived peritoneal membrane from different populations of pigs.
Figure 7:
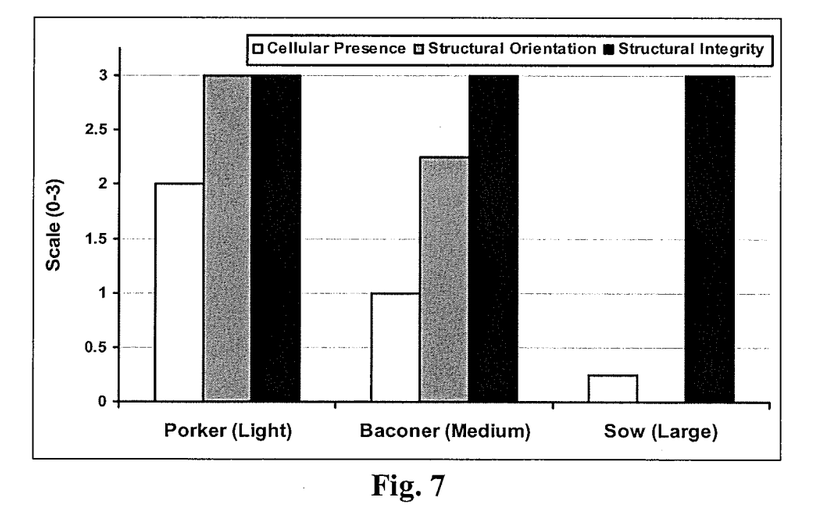
FIG. 7 is a graph showing the cellular presence, structural orientation, and structural integrity of processed porcine peritoneal membranes derived from various populations.

Both human and porcine peritoneal membrane were assessed for suitability and FIG. 5 shows the difference between porcine and human derived peritoneal membrane suggesting that porcine membrane offers better mechanical properties. Characterisation of peritoneal membrane procured from three different porcine populations: Porker, Baconer and Sow was carried out. Membranes from various populations of pigs were analysed for useable surface area and burst strength. It was found that the large (sow derived) membrane offers the largest workable surface area, and the medium (baconer derived) and large (sow derived) membranes offer the highest burst strength in comparison to light (porker derived) membranes. FIG. 5 illustrates the surface area results. FIG. 6 illustrates the mechanical analysis results. FIG. 7 shows the cellular presence and structural properties of the various membranes.

Example 3

Identification of an Appropriate Suturing/Sewing Pattern

Figure 8:
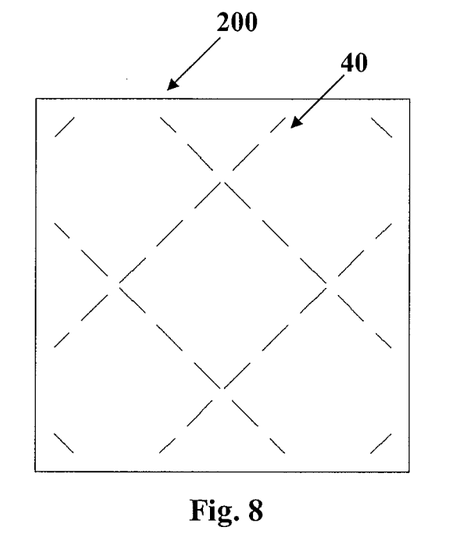
FIG. 8 shows the use of a running suture pattern to create a multilayered peritoneal membrane structure.
Figure 9:
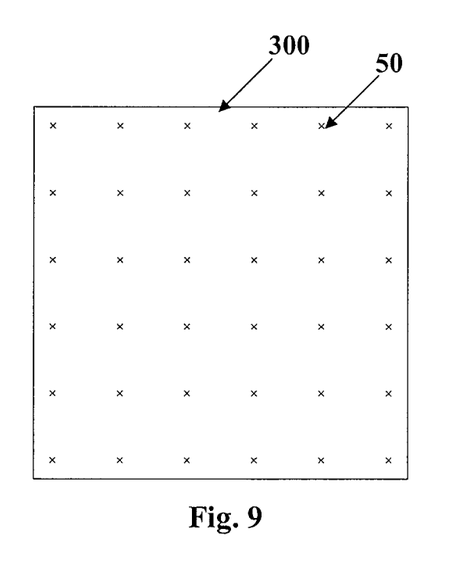
FIG. 9 shows the use of a point suture pattern to create a multilayered peritoneal membrane structure.
Figure 10:
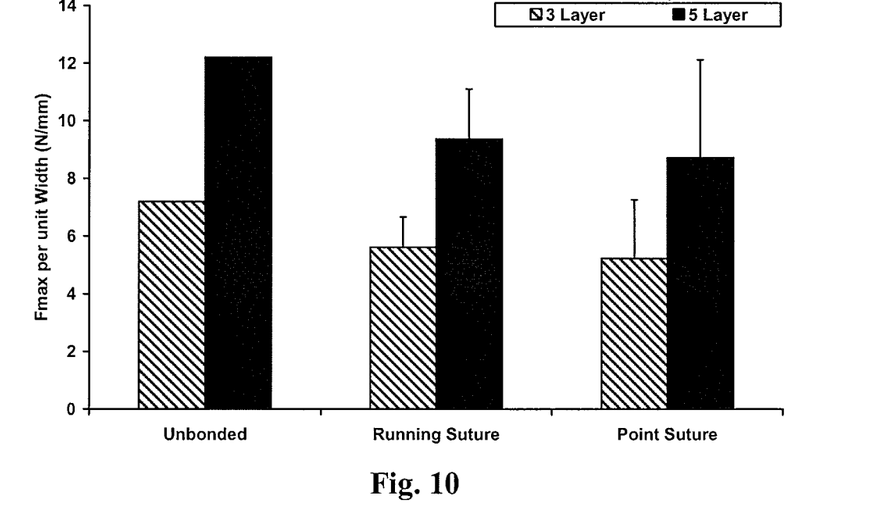
FIG. 10 is a graph showing the variation in the tensile strength of constructs that are unbonded, bonded with a running suture or bonded with a point suture, with values for three- and five-layered peritoneal membrane structures represented.
Figure 11:
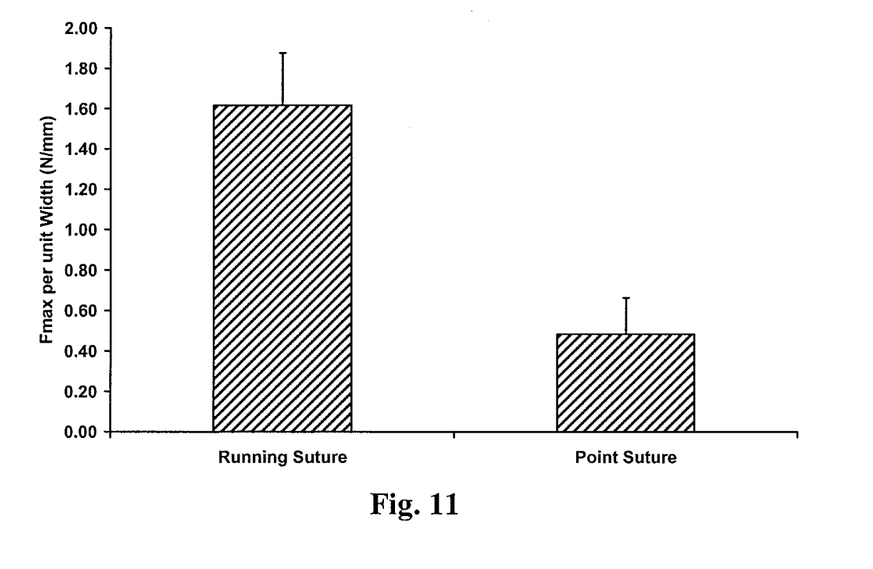
FIG. 11 is a graph showing the difference in bond strength in implants bonded with running sutures and point sutures.
Figure 12:
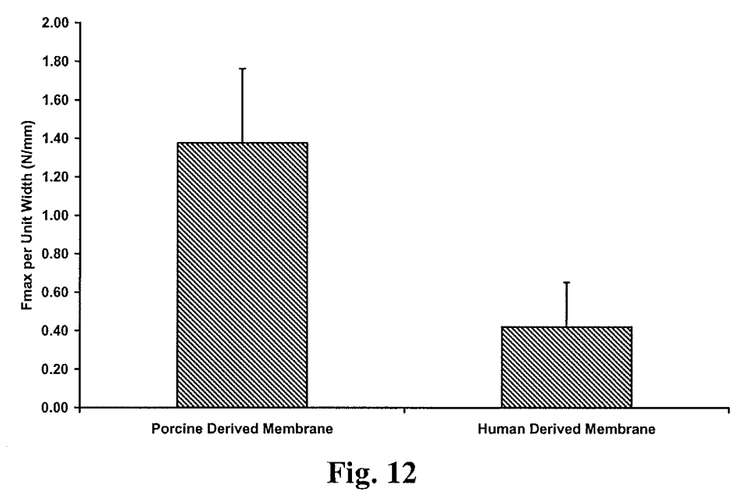
FIG. 12 is a graph showing the difference in mechanical strength between human and porcine peritoneal membrane.

A method of creating a multilayer biological membrane was investigated. The proposed method includes suturing a multilayer membrane structure. The suture retention of single layers of membrane was tested. The compilation of various layers was compared to layers sutured together using running and point suture (see FIG. 8 and FIG. 9). Tensile testing was carried out as well as force required to separate sutured membranes. It was found that no significant difference was found between the tensile properties of the three different arrangements. A running suture was found to have a higher peel force in comparison to point suture. FIG. 10 illustrates the tensile testing results. FIG. 11 illustrates the peel force results.

Example 4

Identification of Alternative Bonding Methods

Instead of forming a sutured peritoneal membrane laminate directly together, the laminate may be achieved through casting and/or crosslinking a solution of pulverized peritoneal membrane tissue onto a membrane followed by placing another membrane over that. Subsequent lyophilisation would use the pulverized material as a penetrating and bridging agent. The pulverized peritoneal membrane may be obtained by decellularizing and lyophilizing the peritoneal tissue first. The lyophilized peritoneal membrane is then mechanically pulverized using any type of mincing device.

Instead of forming a peritoneal membrane laminate directly from the aforementioned methods, the laminate may be achieved through lyophilising multiple layers together. This would involve placing two rough surfaces together under pressure followed by application of adequate lyophilisation parameters to obtain an adequate bond between the layers.

Example 5

Method to Prevent Fluid Build-up Causing Edema

To enhance exudate fluid transport post-repair the following supplementary steps may be performed:

(a) After the laminate has been bonded and lyophilised, the laminate may be perforated throughout to allow for exudates fluid transport. This is recommended in the case of laminates composed of five or more membranes.

(b) Alternatively, the unlyophilised laminate is perforated first, the laminate is then bonded and lyophilised. This is recommended for laminate composed of four or fewer membranes.

The perforations or apertures may be of any size, shape, pattern or density and may be created using mechanical perforation or controlled laser micromachining. In the case where the layers are sutured/sewn together, an oversized suture needle/sewing needle could be used which would create a large perforation to allow fluid transport.

Possible applications for the tissue repair implant of the invention include laparotomy closure/abdominal wall; in general surgery: ventral intraperitoneal hernia repair, or staple line reinforcement; in colo-rectal: abdominoperineal excision of the rectum, or ostomy creation and closure; in urology/gynecology: abdominal/pelvic pain secondary to adhesions, or hysterectomy, myomectomy, and ovariectomy.

The tissue repair implant of the invention reduces or prevents adhesion formation. The peritoneal membrane laminate provides the function of reinforcement and augmentation as a biological scaffold for clinical applications.

The tissue repair implant of the invention acts as a wound reinforcement and template for soft tissue repair in general surgery, colorectal and uro-gynecology.

The peritoneal membrane tissue may be harvested from human donors or animal sources such as bovine or porcine and formed into a laminate as a solution to:

(a) the formation of intestinal adhesions when used as a replacement for synthetic mesh hernia repair, pelvic floor reinforcement, vaginal reconstruction, and other uro-gynecological conditions associated with women's health; and (b) compromised peritoneal membrane as a consequence to a pathology or surgical procedure requiring reinforcement.

The presence of anatomically and physiologically similar tissue when addressing pathologies specifically related to compromised or absent native peritoneal membrane is a viable solution to the shortcomings outlined above in points (a) and (b). Such an approach offers a superior solution to the aforementioned pathologies in comparison to:

(a) synthetic meshes coated with various intestinal anti-adhesive; and (b) biological membranes harvested from alternative anatomical locations such as skin, intestinal submucosa, amniotic membrane.

The peritoneal membrane laminate for reinforcement and augmentation may consist of two classes of products:

(a) human peritoneal membrane products with multiple layers in a 3D scaffold, decellularized, lyophilized, and sterile; and (b) animal source such as bovine or porcine peritoneal membrane product with multiple layers in a 3D scaffold, decellularized, lyophilized, and sterile.

The peritoneal membrane laminate for reinforcement and augmentation is intended as a:

(a) wound covering in general surgery, urology, gynaecology, and colo-rectal; and (b) single means of reinforcement and augmentation in its 3D scaffold form in general surgery, urology, gynaecology, and colo-rectal.

The invention may be provided in a variety of standard and pre-shaped configurations.

The invention provides a biologic membrane laminate based on peritoneal membrane for use as a reinforcing wound covering and preventing adhesion formation while promoting wound healing for intra-abdominal use.

The invention is not limited to the embodiments hereinbefore described, with reference to the accompanying drawings, which may be varied in construction and detail.

What is claimed is:

1. A tissue repair implant comprising a first layer of porcine peritoneal membrane comprising a first mesothelium surface and a second layer of porcine peritoneal membrane comprising a second mesothelium surface, wherein the first and second layers of porcine peritoneal membrane are derived from a porcine sow, and wherein the first layer of peritoneal membrane and the second layer of peritoneal membrane are oriented with the first and the second mesothelium surfaces in an outward direction to generate one or more adhesion-resistant organ contacting surfaces.

2. The implant of claim 1, wherein the first layer of peritoneal membrane is located adjacent to the second layer of peritoneal membrane.

3. The implant of claim 1, wherein the first layer of peritoneal membrane is in direct contact with the second layer of peritoneal membrane.

4. The implant of claim 1, wherein at least one of the layers of peritoneal membrane is non-crosslinked.

5. The implant of claim 1, wherein at least one of the layers of peritoneal membrane is partially crosslinked.

6. The implant of claim 1, wherein at least one of the layers of peritoneal membrane is substantially fully crosslinked.

7. The implant of claim 1, wherein the first layer of peritoneal membrane and/or the second layer of peritoneal membrane is configured to be remodeled by in-growth of tissue.

8. The implant of claim 7, wherein the first layer of peritoneal membrane and/or the second layer of peritoneal membrane is configured to promote in-growth of tissue.

9. The implant of claim 1, wherein the first layer of peritoneal membrane and/or the second layer of peritoneal membrane is configured to promote fluid communication.

10. The implant of claim 1, wherein the first layer of peritoneal membrane and/or the second layer of peritoneal membrane is configured to be attached to an interior wall of an abdominal tissue.

11. The implant of claim 1, wherein the implant is configured to treat an abdominal hernia repair, and/or as a pelvic floor reinforcement, and/or for vaginal reconstruction, and/or as a uterine wound cover, and/or for a colorectal application, and/or for a urological application, and/or for a gynecological application.

12. The implant of claim 1, wherein the shape of the implant is pre-defined to suit the shape of an abdominal cavity.

13. The implant of claim 1, wherein the layer of peritoneal membrane comprises interrupted sutures to retain compliance.

* * * * *